United States Patent [19]
Alter

[11] 3,987,677
[45] Oct. 26, 1976

[54] METHOD AND APPARATUS FOR UNDERGROUND DEPOSIT DETECTION IN WATER COVERED AREAS

[75] Inventor: H. Ward Alter, Danville, Calif.

[73] Assignee: Terradex Corporation, Walnut Creek, Calif.

[22] Filed: Jan. 30, 1976

[21] Appl. No.: 653,991

[52] U.S. Cl. .................. 73/421.5 R; 73/432 R; 23/230 EP
[51] Int. Cl.² .......................................... G01N 1/26
[58] Field of Search ........... 73/421.5, 432 R, 19, 73/170 A; 23/230 EP

[56] References Cited
UNITED STATES PATENTS

| | | | |
|---|---|---|---|
| 2,266,556 | 12/1941 | Kelly | 23/230 |
| 2,918,579 | 12/1959 | Slobod | 250/43.5 |
| 3,455,144 | 7/1969 | Bradley | 23/230 EP |
| 3,561,546 | 2/1971 | Craig | 175/5 |
| 3,681,028 | 8/1972 | Mason | 23/253 |
| 3,714,811 | 2/1973 | Daigle et al. | 73/19 |
| 3,722,271 | 3/1973 | Hovitz | 73/170 |
| 3,862,572 | 1/1975 | Pogorski | 73/432 R |

Primary Examiner—S. Clement Swisher
Attorney, Agent, or Firm—Townsend and Townsend

[57] ABSTRACT

A plurality of gas sample collecting containers are distributed in a predetermined pattern from a vehicle. The containers are cup shaped but weighted so that the open end sinks first and engages the subaqueous earth laer. Gas migrating upwardly through the earth is caught by the inverted cup. The gas sample may be either collected in a separate container or exposed to a detector material located above the expected water level. The sample collecting containers may be retrieved by means of marker floats, magnetic grappling devices or self actuated flotation devices.

47 Claims, 16 Drawing Figures

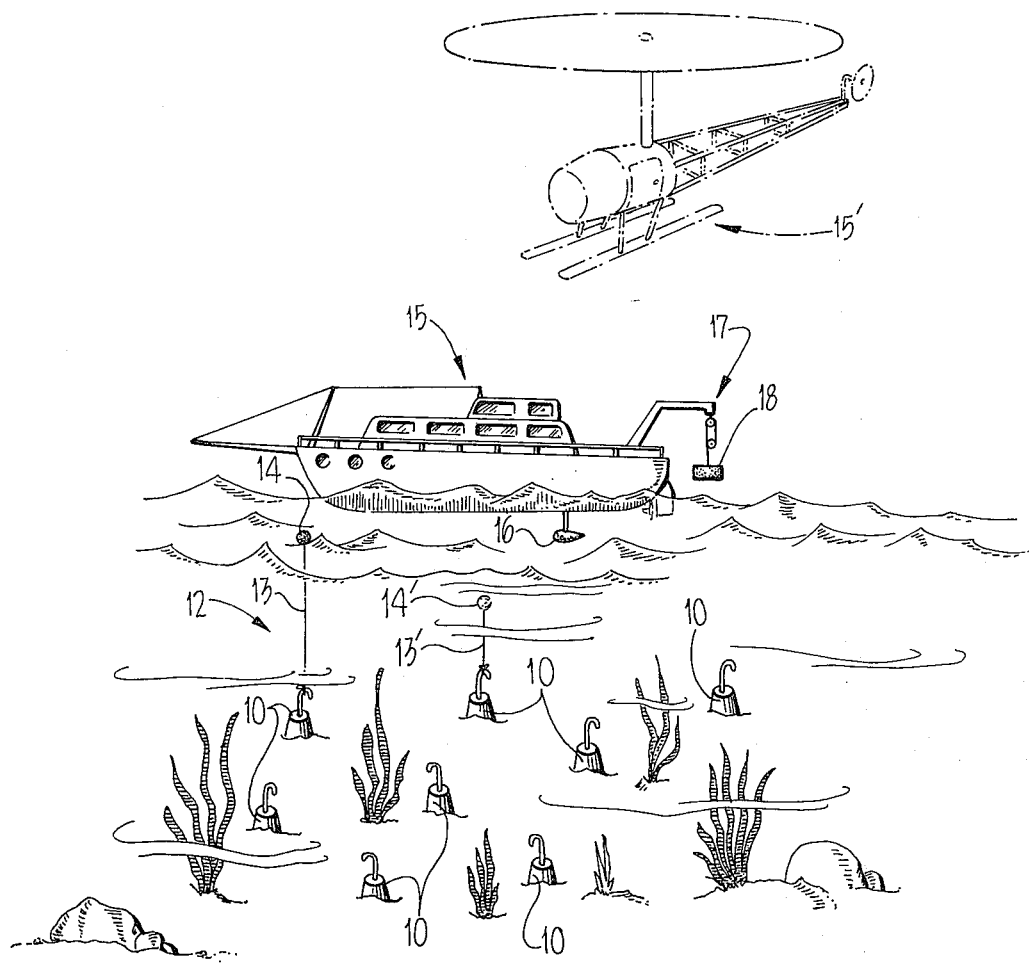
Fig_1
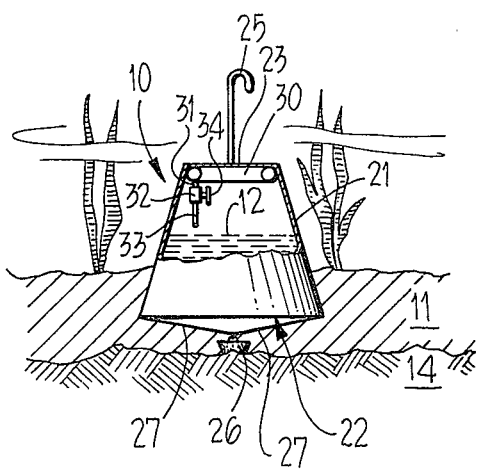
Fig_2
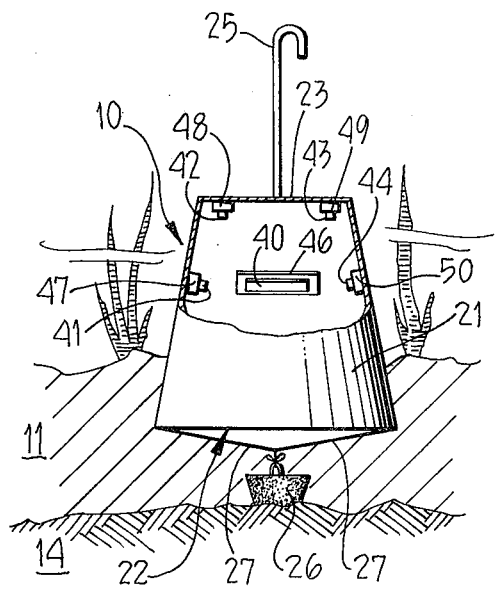
Fig_3

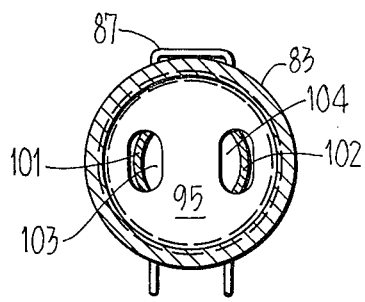
Fig_8
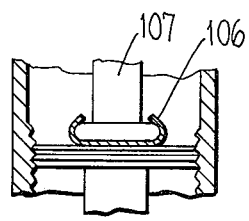
Fig_9
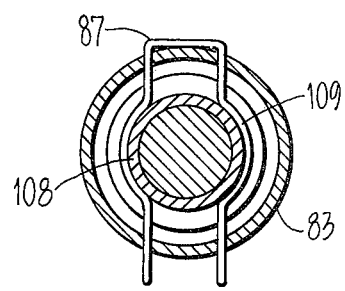
Fig_10
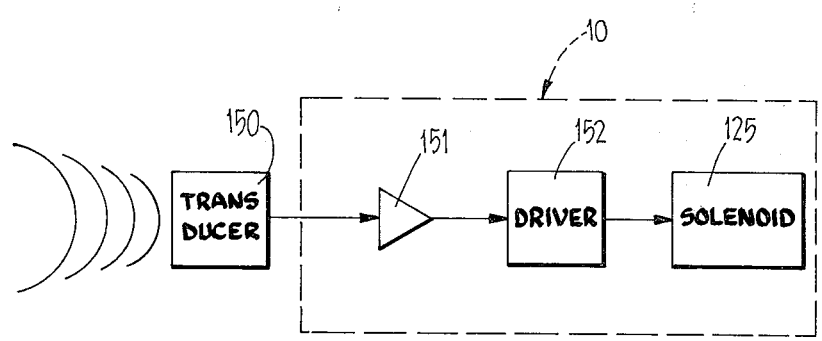
Fig_11
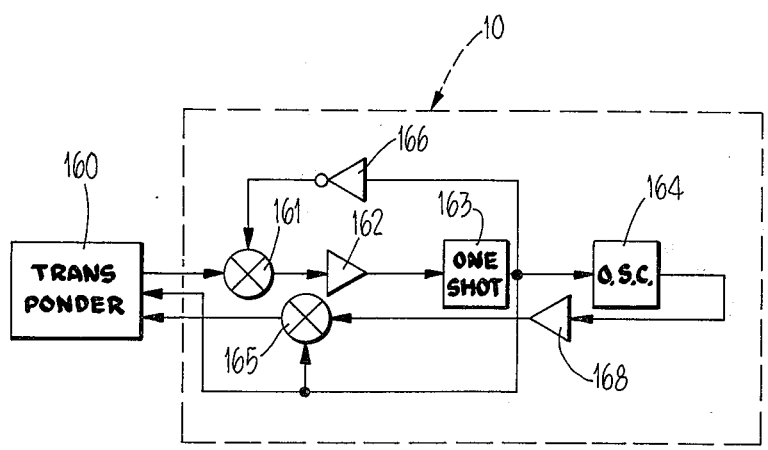
Fig_12

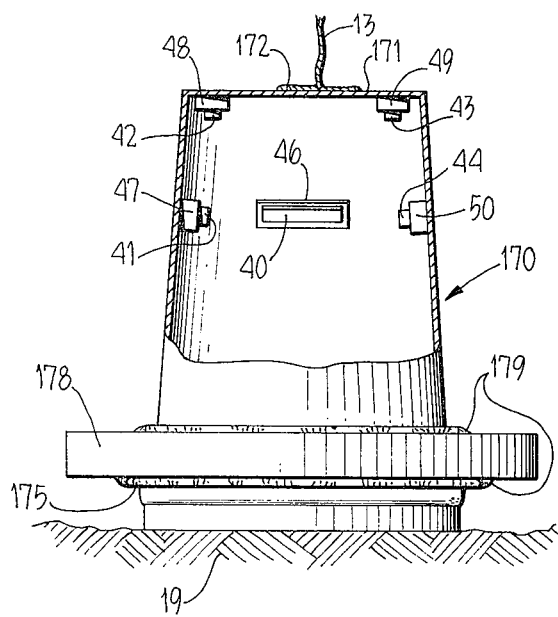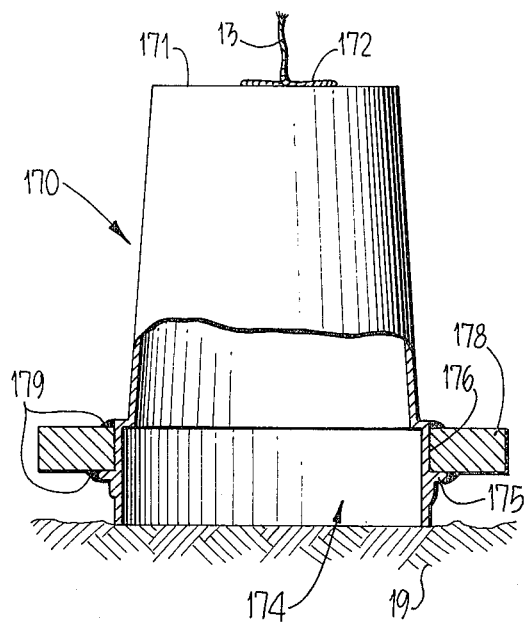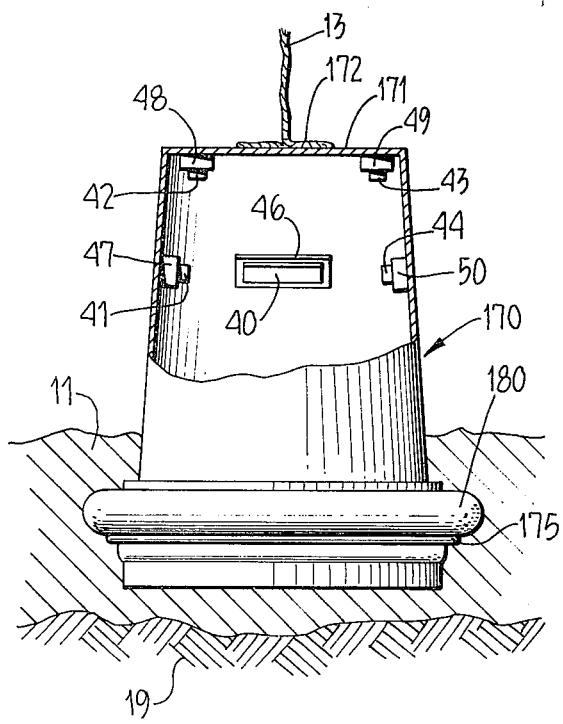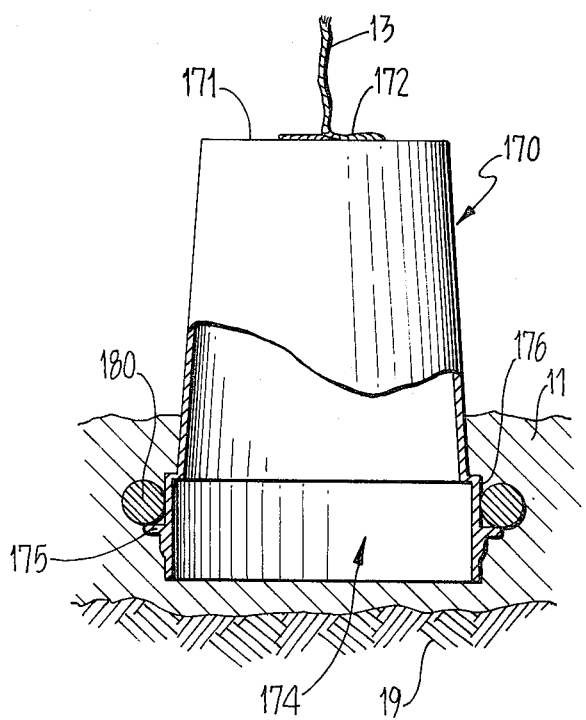

METHOD AND APPARATUS FOR UNDERGROUND DEPOSIT DETECTION IN WATER COVERED AREAS

CROSS-REFERENCE TO RELATED CASES

This application is directed to an improvement of the invention disclosed in copending commonly assigned U.S. Patent Application Ser. No. 545,073 filed Jan. 29, 1975 for "Method and Apparatus For Underground Deposit Detection", the disclosure of which is hereby incorporated by reference.

BACKGROUND OF THE INVENTION

This invention relates to the field of geophysical prospecting. More particularly, this invention relates to an apparatus and method for detecting underground minerals such as oil, gas, coal and other resources located beneath a body of water, such as a lake, pond or ocean. As used in this disclosure, the term "underground minerals" is used to designate both inorganic substances, such as mercury, and uranium, and organic substances, such as petroleum, gas, and coal.

Gaseous substances associated with water-covered subterranean deposits of minerals such as oil, gas and other materials, e.g. mercury and hydrocarbons, are known to migrate upwardly towards the earth's surface and in many cases to escape into the overlying body of water and be dissolved therein. In the past, efforts have been made to sample those gases reaching the earth's surface and those gases dissolved in the water, analyze the samples collected, and generate qualitative and quantitative data in order to locate promising deposits. The following U.S. Patents disclose several sampling devices and methods contrived in the past for this purpose:

|           |           |
|-----------|-----------|
| 2,918,579 | 3,681,028 |
| 3,455,144 | 3,714,811 |
| 3,561,546 | 3,722,271 |

Known techniques represented by the disclosure of the above patents can be generally divided into two categories: techniques for collecting water samples and techniques for collecting sedimentary layer or subsedimentary layer core samples for subsequent analysis of the gaseous constituents therein.

It is now known that the concentration in the overlying water, sedimentary layer and subsedimentary soil of gases whose origins are deep varies significantly with time at any one location. Instantaneous sampling techniques, and sampling techniques utilizing relatively short time intervals, therefore do not yield reliable information relating to the concentration of such gases. In addition, many known techniques require the use of relatively expensive sampling equipment and highly skilled operating personnel, which results in a relatively high cost for obtaining information which is frequently of only marginal use.

SUMMARY OF THE INVENTION

The invention comprises a method and apparatus for collecting gas samples associated with subterranean deposits of a wide variety of underground minerals, such as petroleum, gas, coal, uranium, mercury, and the like, in water covered areas which yields highly accurate information relating to the existence of such underground deposits, and which can be implemented in an extremely inexpensive manner. The method proceeds by planting small gas sample containers from a boat or an aircraft in an inverted position in or on the subaqueous earth layer, determining the container deployment pattern, and obtaining a time-integrated representation of the amount of one or more gases of interest migrating to the earth-water interface over a predetermined time period at each container site. In a first type of container, hereinafter termed a total gas sampler container, all gases migrating upwardly into each container are admitted into a sealed collection chamber at a preselected flow rate. The containers are retrieved from the subaqueous earth layer after the lapse of the predetermined collection interval, and the collected gases are then analyzed in the field or at a remote laboratory by conventional mass spectrographic or gas chromatographic techniques to obtain the relative concentration of specific gases of interest in the total volume of gas collected.

This information is then interpreted to identify potentially valuable deposits of petroleum, gas, or other substances of interest. In a second type of container, hereinafter termed a specific gas sampler container, strips of detector material which are sensitive to predetermined specific gaseous substances associated with underground minerals of interest are mounted within the inverted container and exposed to the upwardly migrating gases over the predetermined time interval to obtain a time-integrated parameter representative of the concentration of the substance of interest. The containers are retrieved from the subaqueous earth layer after the lapse of the time interval, and the detector material alone, or the containers with the detector material still mounted, are taken to the laboratory for qualitative and quantitative analysis.

When sampling with either type of container, each individual container is provided with an identification code which can be correlated with the geographical coordinates of the subaqueous position and the planting time to ensure substantially uniform gas collection periods and to enable correlation of the analytical laboratory results with the individual container locations.

To facilitate planting in the subaqueous earth layer, each individual container is designed to be buoyant in the inverted position and is provided with means for vertically stabilizing the container in the inverted position when the container is placed in the water and for forcing the container to sink to the subaqueous earth layer until the inverted container mouth is either resting thereon or buried therein. After planting, the position of each individual container is determined using conventional sonar techniques, or by incorporating a small sonar transmitter into each individual container for this purpose, the transmitter being actuated either internally or by receipt of an externally originated actuating signal from a nearby ship or aircraft. Alternatively, each container may be provided with a marker line to which a buoyant fishing bobber is attached at or near the surface of the body of water, and the location of the containers may be determined by visual inspection.

After the lapse of the predetermined time interval, the containers are retrieved by conventional mechanical or magnetic underwater grappling devices operated from a boat or aircraft. Alternatively, each container is provided with an automatic retrieval mechanism for floating the container to the surface of the water at the end of the predetermined time interval. In one embodiment of the invention, the retrieval mechanism includes a timing device which is armed when the container is placed in the water and which inflates a balloon or other device after the termination of the predetermined time interval. In an alternate embodiment, the buoyant device is actuated by means responsive to receipt of an actuating signal from a nearby ship or aircraft.

In one specific embodiment of a general purpose container suitable for use as a total gas sampler and a specific gas sampler, the container is provided with a lower volume for receiving increasing amounts of water with increasing depth and an upper volume in which the sampling device is located and which utilizes the increasing pressure of air trapped therein with increasing depth of the container to prevent water from contacting the sampling device.

In an alternate specific embodiment of a general purpose container, a conical container is employed and a sampling device is positioned a predetermined distance from the apex which is less than the distance between the apex and the surface of the water at a prescribed maximum design operating depth. In still another embodiment of a general purpose container, the container has a generally frusto-conical geometrical configuration and the stabilizing means comprises an annular mass received about the outer periphery of the container adjacent the inverted mouth thereof. The annular mass may be fixedly secured to the container, or loosely disposed thereabout and resting on a radially extending peripheral lip.

BRIEF DESCRIPTION OF THE DRAWINGS

FIG. 1 is a schematic pictorial view illustrating deployment of containers according to the invention;

FIG. 2 is a sectional view showing an underwater total gas sampler container in situ;

FIG. 3 is a sectional view showing an underwater specific as detector container in situ;

FIG. 7 is a sectional view taken along lines 7—7 of FIG. 6;

FIG. 8 is a section view taken along lines 8—8 of FIG. 7;

FIG. 9 is a sectional view taken along lines 9—9 of FIG. 7;

FIG. 10 is a sectional view taken along lines 10—10 of FIG. 7;

FIG. 11 is a block diagram of an alternate automatic floatation arrangement;

FIG. 12 is a block diagram of an automatic sounding device for enabling location of an underwater sampling container;

FIGS. 13 and 14 are side elevational views partially broken away illustrating an alternate embodiment of an underwater sampling container; and FIGS. 15 and 16 are side elevational views partially broken away illustrating another alternate embodiment of an underwater sampling container.

DESCRIPTION OF THE PREFERRED EMBODIMENTS

Figure 4:
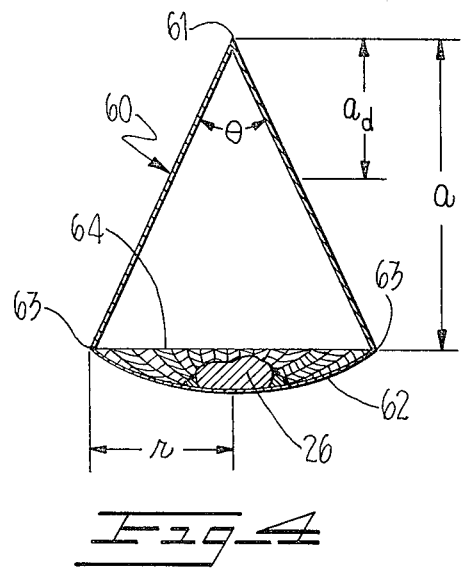
FIG. 4 is a sectional view of a first embodiment of an underwater sampling container housing designed for use to specific depths.

Turning now to the drawings, FIG. 1 is a pictorial schematic view illustrating the invention. As seen in this Fig., a plurality of small gas sample containers 10 are situated in the sedimentary layer 11 (see FIG. 2) underlying a body of water 12. For illustrative purposes the physical size of gas sample containers 10 is greatly exaggerated. Attached to each of containers 10 by means of a flexible line 13 is a small float 14 such as a fishing bobber, which serves to demarcate the location of the associated container. Float 14 may be attached to associated container 10 by a line 13 having sufficient length to permit float 14 to rest on the surface of body of water 12, or a shorter line 13' which causes the bobber 14' to be held below the surface of the body of water 12 by the superior weight of the associated container 10.

FIG. 2 is a sectional view showing a first embodiment of an underwater sampling container 10 configured as a total gas sample container in situ. Total gas sample container 10 has a generally frusto-conical shape with a sidewall portion 21 terminating in an open mouth 22, and a closed end portion 23. Attached to closed end portion 23 and extending externally thereof is a hook-like member 25 provided for handling purposes to be described and preferably fabricated from a magnetizable material. Attached to the open mouth 22 end and depending downwardly therefrom is a weight 26 secured to container 10 at or adjacent open mouth 22 by means of a flexible attachment means, e.g. flexible lines 27. The weight 26 may be tapered as shown, or may be configured as a sphere, spheroid or other shapes. For small containers, common fishing sinkers may be used.

Secured to the interior of total gas sample container 10 adjacent closed end portion 23 is partially evacuated toroidal tank 30 having an inlet 31 coupled to the outlet of a conventional metering valve 32 having an inlet 33 in communication with the interior volume of the container 10, and a manually operable adjustment knob 34 which enables valve 32 to be opened and closed. For equivalent tank configuration, reference should be had to the above-noted co-pending patent application.

As shown in FIG. 2, the mouth 22 of container 10 is embedded in soft sedimentary layer 11 to define an enclosed volume for containing any gases which migrate upwardly through sedimentary layer 11 from the earth's crust 19. Trapped within the internal volume of container 10 is a quantity of water 12. The upper level of water 12 lies below the mouth of inlet 33 so that only gases are admitted into the evacuated interior of tank 30 when valve 32 is open and container 10 is lodged in situ. The physical dimensions of container 10 required to ensure that inlet 33 always lies above the level of water 12 is dependent upon the depth of sedimentary layer 11 below the surface of the body of water. For example, if sedimentary layer 11 is at a depth of thirty feet below the surface, and container 10 has a height of 2 feet (measured between open-mouth 22 and closed portion 23) defining an internal volume of two cubic feet the mouth of inlet 33 should be arranged no more than 1 foot below closed end portion 23 to avoid contact with the water 12 trapped in the interior of container 10. In practice, container 10 is typically designed for use at a maximum depth and is preferably marked accordingly.

FIG. 3 illustrates an underwater sampling container 10 configured as a specific gas sample container. As seen in this Fig., a plurality of specific gas detectors 40-44 are secured to the inner wall surfaces of cup 10 at a location above the level of water 12 at the working depth by means of suitable mounting members 46–50. The choice of individual specific gas detectors 40–44 depends upon the specific gases to be detected over the collection period, and reference should be had to the above referenced patent application for specific examples.

Containers 10 are deployed in the water from either a surface vessel 15 shown in FIG. 1 or a suitable aircraft, e.g. a helicopter 15'. To deploy from a surface vessel 15, a quantity of containers 10, configured as either a total gas sample container or a specific gas sample container, or a mix of both types, are placed on board the vessel 15 and transported to the survey site. As the vessel 15 proceeds along surface of the body of water, individual containers are placed overboard, preferably at regular intervals. As each container 10 is released into the water 12, it descends under its own weight to the sedimentary layer 11. As each container 10 descends to sedimentary layer 11, weight 26 and flexible cord 27 maintain the container 10 in the inverted attitude illustrated so that the air trapped therein cannot be displaced by the water 12 but merely compressed. When the container 10 reaches sedimentary layer 11, it is partially embedded therein due to the momentum provided by the combination of its own mass and the mass of weight 26. When planted in situ, a quantity of water 12 is trapped within the internal volume of container 10, as illustrated in FIGS. 2 and 3.

It should be noted that the combined mass of container 10 and weight 26 must exceed the weight of the water displaced by these elements and the buoyant force provided by bobber 14 in order to ensure that the container descends to the water-earth interface. In addition, weight 26 must be attached to container 10 in such a manner that the assembly is hydrodynamically stable so that container 10 maintains the inverted attitude during the downward descent. This condition may be assured by securing the weight 26 directly to the rim of the open mouth 22 or adjacent thereto by a flexible support, such as cords 27. Other equivalent attachment arrangements are a flexible net attached to open mouth 22 at the rim, elastic bands arranged in a substantially identical manner to lines 27, springs secured to the rim of open mouth 22 at one end and to weight 26 at the other end, the annular weight shown in the embodiments illustrated in FIGS. 13–16 and described below, and other suitable arrangements known to those skilled in the art.

Once all containers 10 required for a given survey have been planted, their respective locations are determined by observing bobbers 14 from the vessel. If desired, the bobbers and container locations may be determined by activating a vessel-mounted conventional sonar transponder 16 as vessel 15 traverses the survey site. In deep water locations where the use of bobbers 14 is impractical containers 10 may be located using conventional sonar techniques. Alternatively the individual containers 10 may be provided with a transponding device, described below, which is activated by a signal from the vessel.

After the predetermined time interval has elapsed, the containers 10 are retrieved by traversing the survey area and withdrawing each container 10 manually by bobber 14 and line 13. For submerged bobbers, and in deep water locations not employing bobbers 14, the containers may be retrieved by operating a winch and boom assembly 17 to lower a conventional mechanical or magnetic grappling device 18 into the water 12. As the grappling device 18 traverses the survey site, the individual containers 10 are secured thereto by hooked members 25 and are raised to the surface of the water 12 by operating the winch and boom assembly 17.

While the containers 10 illustrated in FIGS. 2 and 3 may be designed for use at any depth, in practice frustoconical containers of this type are preferred for use in relatively shallow planting applications, e.g. those depths at which the hydrostatic pressure does not exceed 15 pounds per square inch (approximately 30 feet). For those applications requiring planting at a greater depth, underwater sampling containers having the modified construction as illustrated in FIGS. 4 and 5 are preferred.

Figure 5:
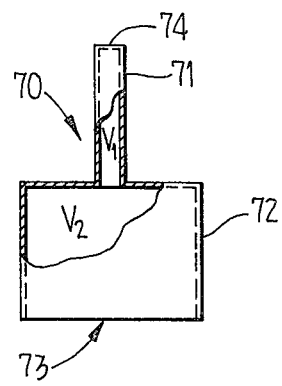
FIG. 5 is a sectional view of a second embodiment of an underwater sampling container housing designed for use to specific depths.

With reference to FIG. 4, a conical container 60 having an upper apex angle $\Theta$, an altitude $a$ and radius $r$ is provided with a weight 26 which is attached to the upper surface of a flexible net 62 fabricated from string, nylon or the like and attached to the rim portion 63 of the open mouth 64 of container 60. To ensure that the level of water 12 does not rise to the level of the sampling device or detector, a dry altitude $a_d$ is determined for container 60 by the following formula:

$$a_D = a \left( \frac{P_O}{P_X} \right)^{1/3} \quad (1)$$

where Po, Px are atmospheric and hydrostatic pressures, respectively. The level to which the water will rise in container 60 can thus be calculated from the ratio of the atmospheric pressure to the pressure at a given depth using formula (1). Once the maximum operating depth has been selected, the value of the hydrostatic pressure at that depth may be obtained from a pressure table, the ratio Po/Px determined, and the value of $a_D$ calculated for a container 60 of altitude $a$. The inlet of the total gas sampler or the specific gas detector material is then mounted within container at or above $a_D$, the dry altitude.

To illustrate, at a depth of 600 feet, the ratio of $P_o$ to $P_x$ is 0.05 and the cube root of this ratio is 0.37. For a container having an altitude $a$ of 12 inches, $a_D$ is 4.44 inches. The inlet of a total gas sampler or the lower edge of the specific gas detector is located within container 60 less than 4.44 inches from apex 61 to ensure no contact with water.

FIG. 5 shows a second embodiment of a modified under-water sampling container 70 having an upper substantially cylindrical portion 71 with an upper internal dry volume $V_1$, and a lower substantially cylindrical portion 72 terminating in an open mouth portion 73. In this embodiment, the sampling elements are installed in the upper dry portion with volume $V_1$, and the relative ratios of the volumes $V_1$ and $V_2$ are selected such that the water 12 trapped in the internal container volume cannot rise to the level of the sampling elements located in volume $V_1$ at the maximum depth to which the container is designed for use. For example, if the container 70 is designed for use at a maximum depth of 600 feet below the surface of the body of water 12, the container is dimensioned so that the ratio of volume $V_2$ to volume $V_1$ is 20, which insures that the water 12 trapped within the container can never enter volume $V_1$.

Figure 6:
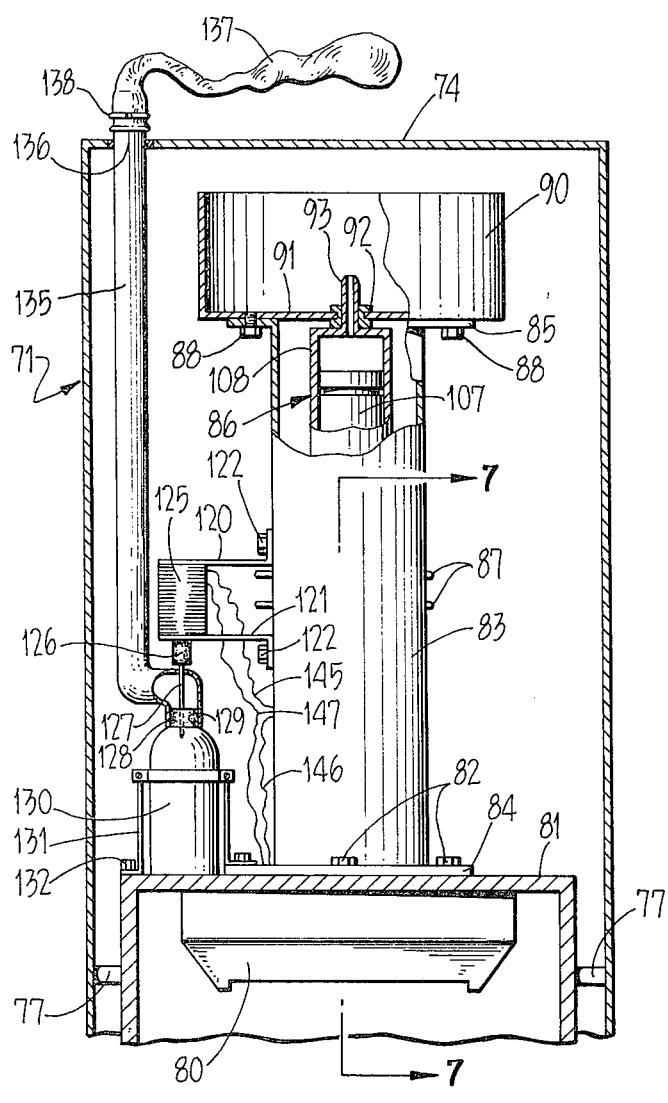
FIG. 6 is a partial side elevational view of an underwater sampling container provided with an automatic floatation device.

In some applications, it is preferable that the container be automatically floated to the surface of the body of water 12 after the predetermined sample period has elapsed. FIGS. 6–10 illustrate an underwater sampling container of the type generally illustrated in FIG. 5 provided with a self-timing automatic floatation device. With reference to FIG. 6, upper cylindrical portion 71 of container 70 includes an electrical clock mechanism 80 mounted in a base member 81, member 81 being secured to housing 71 by a pair of oppositely extending arms 77 secured to housing 71 by any suitable means such as welding. Clock mechanism 80 is powered by a battery (not shown) which may be contained within the clock housing or mounted to element 71. Secured to the upper surface of base member 81 by means of capscrews 82 is a substantially cylindrical housing member 83 having flanged end portions 84, 85. Electrical clock mechanism 80 may comprise any one of a number of known mechanisms, such as a General Electric Model XC68 X134 clock motor.

A conventional hypodermic syringe 86, partially visible in FIG. 6, is secured within the interior of housing 83 by means of a pair of pin fasteners 87 in the manner described below. Secured to the upper end of housing 83 by means of capscrews 88 is an open-mouthed substantially cylindrical cup-like member 90 having a bottom wall 91. Bottom wall 91 has a central aperture provided with a seal 92 through which the apertured tip 93 of syringe 86 extends to enable ingress of gas accumulating in the interior of member 90 to the interior of syringe 86.

With reference to FIG. 7, the interior of housing member 83 is internally threaded along a lower portion 94 thereof, and an externally threaded follower nut 95 is threadably engaged therein. Attached to the output shaft 97 of clock mechanism 80 by means of a nut 98 is a rotatable spider member 100 having a pair of upwardly extending arms 101, 102. As best shown in FIG. 8, arms 101, 102 are received in a pair of oppositely arranged apertures 103, 104 of follower nut 95 so that rotation of spider member 100 is transmitted to follower nut 95.

Secured to the upper surface of follower nut 95 by means of a mounting clip 106 is the axially translatable inner element 107 of syringe 86. The stationary outer element 108 (FIG. 6) is maintained in a relatively fixed attitude relative to inner element 107 by means of a pair of conventional retaining clips 87 each comprising a generally U-shaped member having a pair of arms with a curved intermediate portion 109 (FIG. 10) for embracing the outer wall surface of outer syringe element 108 above and below, respectively, lower flange member 110, each pin being received in two pairs of oppositely disposed apertures formed in housing member 83.

In order to provide a limit stop for follower nut 95 in the downward direction, housing member 83 is provided with a transverse bore 112 having an electrically insulative insert 113 in which a mechanical stop member 114 is engaged. Limit stop member 114 has an inner end which extends radially inwardly sufficient distance to provide abutting contact with the lower surface of follower nut 95 when the latter element has reached the desired lower limit of travel.

Mounted externally of housing member 83 but internally of housing portion 71 by means of a pair of brackets 120, 121 and bolts 122 is a conventional electrically operated solenoid 125 having a plunger 126 normally engaged with a pin 127. Pin 127 has a pointed end engaged in surface contact with a closure disk 128 which normally seals the neck 129 of a conventional compressed air cartridge 130 which is secured to base member 81 by means of mounting brackets 131 and bolts 132.

Neck 129 of compressed air cartridge 130 is sealingly secured to the first end of a fluid conduit 135, the remaining end 136 of which passes through the enclosed end portion 74 of member 71. Sealingly secured to end 136 of fluid conduit 135 is an inflatable elastic member 137, e.g. a rubber balloon, attached thereto by means of an appropriate spring clip 138 or the like and adapted to be inflated whenever pin 127 ruptures closure disk 128 of compressed air cartridge 130.

With reference to FIG. 7, a solenoid actuating circuit is provided which includes a switch 140 mounted internally of mechanical stop member 114. Switch 140 includes a movable actuating arm 142 extending radially inwardly of housing 83 a sufficient distance to be deflected downward by traveling nut 85 to close switch 140. A first conductor 145 coupled to one contact of switch 140 is coupled to a first end of the coil portion of solenoid 125. A second conductor 146 coupled to the other contact of switch 140 is coupled to one terminal of the battery contained in clock assembly 80. An additional conductor 147 is coupled between the other terminal of the battery in housing 80 and the coil portion of solenoid 125.

In operation, with nut 95 initially positioned adjacent the upper limit of threaded portion 94, output shaft 97 is rotated by clock mechanism 80. This movement is transmitted via arms 101, 102 to follower nut 95 causing nut 95 to be translated in an axially downward direction of housing member 83. As follower nut 95 is rotated and translated, inner syringe element 107 follows the motion of nut 95 resulting in the gradual withdrawal of inner syringe element 107 from outer syringe element 108. The gradual withdrawal of inner element 107 draws the gasses accumulating in inlet member 90 through the tip 93 of syringe 86 and into the collecting chamber internal thereto. This operation continues until nut 95 reaches the downward limit of travel, thereby forceably terminating further withdrawal of inner syringe element 107 and causing solenoid 125 to be actuated by closure of the switch 140. When solenoid 125 is actuated, plunger 126 forces pin 127 to the extreme downward position illustrated in FIG. 6, thereby rupturing closure disk 128 and permitting the compressed air contained in cartridge 130 to escape via conduit 135 into inflatable member 137. Member 137 expands until the volume of water displaced thereby exceeds the weight of the water displaced by the entire underwater sampling container, after which the container becomes buoyant and floats to the surface of body of water 12. Once at the surface, container 70 may be retrieved from either a surface vessel 15 or an aircraft 15' by conventional techniques.

It should be noted that, although underwater sampling container 70 is specifically shown as incorporating a total gas sampler mechanism, container 70 may also be configured as a specific gas detector, if desired.

In addition, the self-timing automatic floatation mechanism of FIGS. 6–10 may be modified by one of ordinary skill in the art and employed with underwater sampling containers of the type shown in FIGS. 2–4.

FIG. 11 is a block diagram of an alternate arrangement which enables an individual container to be released for floatation to the surface in response to a receipt of a remotely generated command signal. As shown in this Figure a conventional transducer 150 capable of generating electrical output signals in response to the receipt of acoustic signals of a given frequency is mounted externally of a container 10. The electrical output of transducer 150 is coupled via an amplifier 151 to the input of a conventional solenoid driver circuit 152. The output of drive circuit 152 is coupled to the coil portion of solenoid 125. Electrical power is supplied to the several circuit elements by a conventional battery (not shown).

In operation, in response to the receipt of a remotely generated acoustical signal, the output of transducer 150 is amplified and used to control driver circuit 152 to actuate solenoid 125. Once actuated, solenoid 125 ruptures closure disk 128 of compressed air cylinder 130 to inflate member 137 and float the container 10 to the surface of the water 12. This arrangement may be preferred in applications in which a surface vessel or helicopter is not normally present at the end of a predetermined sample interval.

FIG. 12 is a block diagram of a remotely actuated unit adapted to be used for accurately pinpointing the location of individual containers 10. A conventional transponder 160 is coupled via a first electronic transfer switch 161 and an amplifier 162 to the input of conventional one-shot circuit 163. The output of one-shot circuit 163 is coupled directly to the input of an oscillator 164 having a characteristic frequency unique to the network of containers or a specific container and also to the control terminal of a second electronic transfer switch 165. The output one one-shot 163 is also coupled via an inverter 166 to the control terminal of first electronic transfer switch 161, and to the control input of transponder unit 160, which is normally in the receive mode. The output of oscillator 164 is coupled via an amplifier 168 to the transfer input terminal of electronic switch 165, the output of which is coupled to the transmit input of transponder 160.

In operation, when an enabling acoustic signal is received by transponder unit 160, one-shot circuit 163 is triggered to the metastable state for the predetermined time-out period thereof. When one-shot 163 is in this state, switch 161 is disabled, switch 165 is enabled, and transponder 160 is placed in the transmit mode. In addition, oscillator 164 is activated, so that the output thereof is coupled to the transponder 160 which transmits an acoustic signal to a remote receiver located on vessel 15 or suspended into the body of water 12 from aircraft 15'. The received signal is processed using conventional techniques to pinpoint the location of the associated container 10.

FIG. 13 and FIG. 14 illustrate an alternate embodiment of an underwater sampling container generally designated by reference numeral 170 and which may be configured as either a specific gas detector with elements 40–44, 46–50 as shown or a total gas sampler with elements 30–34 as shown in FIG. 2 or their equivalent. In this embodiment, marker line 13 is adhered to the outside surface of bottom wall 171 by the simple expedient of a waterproof adhesive tape 172. Tape 172 may comprise any one of a number of known commercially available products, e.g. "Bear" Tape available from the Norton Company.

As best shown in FIG. 14, the outer surface of the sidewall of container 170 adjacent open-mouthed portion 174 thereof is provided with a peripheral flange 175 and a flatted wall surface 176 for receiving a toroidal weight 178, with the inner portion of the lower surface of weight 178 resting on flange 175. Weight 178 is secured to container 170 by means of a suitable waterproof cement 179. Toroidal weight 178 provides hydrodynamic stability to container 170 in its descent to the earth-water interface.

FIGS. 15 and 16 illustrate another alternate embodiment of a gas sample container 170, similar to that depicted in FIGS. 13 and 14 but having a toroidal shape weight 180 with a circular cross section as shown. In this embodiment, weight 180 is received on flange 175 and no adhesive or cement is employed. It is understood that either weight 178 or weight 180 may be permanently adhered to container 170 or merely disposed about flatted surface 176 without any adhesive means in accordance with the following requirements.

In some areas where the earth water interface is devoid of a silt layer, such as depicted in FIGS. 13 and 14, it may be desirable to permanently adhere the toroidal weight 178 to the container 170, both to facilitate handling before planting and after retrieval and also to prevent loss of a weight 178 in the event that container 170 comes to rest in a position of unstable equilibrium at the bottom of the body of water. The latter could occur for example, if one edge of the open-mouth end 174 of container 170 were to come to rest on a large stone or rock while the diagonally opposite edge came to rest on the bottom. In such an event, adhesive 179 would prevent toroidal weight 178 from slipping back down toward end 171 and being lost.

In those areas overlying an earth-water interface having a silt layer 11 overlying hardpan 19, it may be preferable to merely slip toroidal weight 180 onto container 170 prior to placing container 170 in the water for its downward descent. As container 170 strikes the silt layer 11, and begins to burrow therein, weight 180 assists this downward motion of container 170 into silt layer 11. However, the distance that container 170 will burrow into silt layer 11 will depend to a great extent on the surface area of toroidal weight 180 and the density of the silt layer 11: thus, weight 180 will exhibit a tendency to control the depth of penetration of container 170 into silt layer 11.

Both weights 178 and 180, and the container wall structure including flange 175 and wall surface 176 permit rapid assembly of the weight plus cup and thus are preferred for at least shallow water applications over the embodiment shown in FIGS. 2–4. It should further be noted, that the toroidal weight embodiments of FIGS. 13–16 are ideally suited for use in water-filled bore hole environments in which the silt layer 11 comprises soft mud.

In all embodiments of the invention, a network of containers 10 is planted, with each container in a different coordinate position in sedimentary layer 11. After planting, the exact location of each container is determined and correlated to the individual containers by a suitable coding system. After the containers have been left in situ for the predetermined sampling period, they are retrieved and the collected gas or the exposed detector strips are subjected to suitable qualitative or quantative analyses in accordance with any of a number of known techniques. In all cases, a time integrated representation of each particular gas of interest is obtained by closely controlled the duration of the exposure or collection period. It should be noted that the duration of the exposure or collection period may vary from survey to survey within a range from about one week to about two months, the duration of the sampling period being dependent upon a number of factors including the total number of individual containers employed in a particular survey, the mutual spacing of the containers, and the speed with which the individual containers may be planted and retrieved. In any event, the sampling period should be long compared to the period of the time varying signal of gas evolved from the earth. It is important to note that care should be exercised to ensure that the length of the collection period is substantially identical for each collector in a given survey.

As will now be apparent, the invention provides a simple and inexpensive technique for obtaining extremely valuable and reliable information relating to the existence of underlying deposits of a wide variety of oil, gas, coal and other mineral resources in water covered areas. Surveys may be conducted according to the invention on a relatively wide scale quickly and economically. It is further noted that the invention is extremely flexible in that it may be specially adapted to the type of underground minerals being sought by simply selecting specific gas detectors which are only sensitive to those gases associated with the sought underground mineral. It should also be noted that the invention may be employed in areas of the earth's surface covered by other fluids, such as marshy or swampy areas covered by mud, areas covered by muskeg and the like.

A particularly useful application of the invention can be made to mineral prospecting in cold climates in which the body of water overlying the area to be surveyed is covered with ice. In such regions, the survey may be conducted by simply cutting a hole in the ice layer with an ice auger at each container planting site, lowering a container by means of marker line 13 through the hole in the ice, and permitting the hole to freeze over with the float 14 or any other suitable marker, e.g. a small flag attached to the marker line, above the surface of the ice. After the predetermined sampling period, each container may be readily located by noting the marker, and may be retrieved by simply removing the ice about the marker line and hauling in the marker line by hand. Containers of the type shown in FIGS. 13–16 are ideally suited for such applications since the torous weights 178, 180 and the marker line 13 may be quickly and easily installed on the container 170.

While the above provides a full and complete disclosure of the preferred embodiments of the invention, various modifications, alternate constructions and equivalents may be employed without departing from the true spirit and scope of the invention. For example, the toroidal shape of tank 30 of FIG. 2 is illustrative only, and other equivalent tank shapes such as those disclosed in the above-referenced patent application may be employed, as desired. Similarly the shapes of containers 10, 60 and 70 are illustrative only and other variant shapes may be used. Also, the manually operable valve 32 illustrated in FIG. 2 may be replaced by a remotely actuated valve and appropriate acousto-electronic circuitry similar to that shown in FIG. 11 included in container 10 to enable remote actuation of the valve from a vessel 15 or aircraft 15'. In addition, other mechanisms than that shown in FIGS. 6–10 may be employed to inflate an elastic member and float the containers 10 to the surface of body of water 12. Therefore the above description and illustrations should not be construed as limiting the scope of the invention which is defined by the appended claims.

What is claimed is:

1. A method of geophysical prospecting for underground minerals in earth regions underlying a fluid body, said minerals having specific gases associated thereto, said gases normally migrating to the surface of said earth regions, said method comprising the steps of:
  a. Depositing a plurality of open-mouthed gas sample containers at the bottom of said fluid body, each container resting in an inverted position on the surface of the earth region below said fluid body and including means for obtaining a time integrated parameter representative of at least one of said gases;
  b. Permitting said containers to remain at said bottom for a predetermined time period to enable said means to obtain said time integrated parameter representative of at least one of said gases migrating into said container over said time period; and
  c. Retrieving said containers from said bottom after said predetermined time period has elapsed for subsequent analysis of said parameter.

2. The method of claim 1 wherein said time integrated parameter is obtained by collecting said gases in a sample chamber in each said container at a predetermined controlled rate.

3. The method of claim 1 wherein said time integrated parameter is obtained by exposing at least one specific gas detector mounted in each said container for said predetermined time period.

4. The method of claim 1 wherein said bottom of said fluid body includes a sedimentary layer and said step (a) of depositing includes the step of permitting the mouths of said containers to be embedded in said sedimentary layer.

5. The method of claim 1 wherein said step (a) of depositing includes the step (i) of placing said containers in said fluid body in an inverted attitude, and (ii) permitting said containers to sink to said bottom while maintaining said inverted attitude.

6. The method of claim 5 wherein said step (i) of placing is performed from a vessel at least partially immersed in said fluid body.

7. The method of claim 5 wherein said step (i) of placing is performed from an airborne aircraft.

8. The method of claim 1 wherein said step (a) of depositing is followed by the additional step of locating the geographical coordinates of said containers at said bottom.

9. The method of claim 8 wherein said step of locating includes the steps of transmitting acoustic signals in said fluid body to said containers and detecting acoustic signals reflected from said containers.

10. The method of claim 8 wherein said step of locating includes the steps of activating acoustic signal generators carried by said containers and detecting the acoustic signals generated thereby.

11. The method of claim 10 wherein said step of activating is performed at a location remote from said containers.

12. The method of claim 8 wherein said step of locating includes the step of adhering a marker line to each of said containers prior to said step (a) of depositing and observing the location of said marker line after said step (a) of depositing.

13. The method of claim 12 wherein said step (c) of retrieving includes the step of raising said containers with said marker lines.

14. The method of claim 1 wherein said step (c) of retrieving includes the steps of lowering a grappling device into said fluid body, attaching said containers to said grappling device, and raising said grappling device to the surface of said fluid body with said containers attached thereto.

15. The method of claim 1 wherein said step (c) of retrieving includes the step of causing said containers to float to the surface of said fluid body.

16. The method of claim 15 wherein said step of causing said containers to float includes the step of activating floatation devices carried by said containers.

17. The method of claim 16 wherein said floatation devices are individually responsive to an acoustic signal and wherein said step of activating is performed by generating said acoustic signal at a location remote from said container.

18. The method of claim 17 wherein said location comprises the position of a vessel at least partially submerged in said fluid body.

19. The method of claim 17 wherein said location comprises the position of an airborne aircraft.

20. For use in a method of geophysical prospecting for underground minerals in earth regions underlying a fluid body, said minerals having specific gases associated thereto, said gases normally migrating to the surface of said earth region: an open-mouthed gas sample container having side and bottom walls and adapted to rest on the surface of said earth region beneath said fluid body in an inverted attitude to trap said gases therein, said gas sample container including means for obtaining a time-integrated parameter representative of said gases migrating there-into over a predetermined time period, and means for maintaining said gas sample container in said inverted attitude.

21. The combination of claim 20 wherein said means for obtaining a time integrated parameter includes a gas collection chamber having an inlet in communication with the interior of said chamber and a volume defined by the interior of said container, and means for admitting said gases into said chamber at a predetermined flow rate.

22. The combination of claim 21 wherein said admitting means comprises metering means coupled to said inlet and means for drawing said gases through said metering means at said predetermined rate.

23. The combination of claim 22 wherein said drawing means comprises a vacuum provided within said chamber.

24. The combination of claim 22 wherein said metering means comprises a tubular conduit coupled to said inlet and including a metering valve.

25. The combination of claim 20 wherein said means for obtaining a time integrated parameter includes at least one specific gas detector mounted within the volume defined by said container.

26. The combination of claim 20 wherein said means for maintaining includes a tapered mass and flexible means for suspending said mass below the center of gravity of the assembly comprising said container and said mass when said container is in said inverted attitude.

27. The combination of claim 26 wherein said flexible means is attached to said container adjacent the open mouth thereof.

28. The combination of claim 26 wherein said mass is tapered inwardly in the downward direction when said container is in said inverted attitude.

29. The combination of claim 26 wherein said flexible means comprises a net and said mass is supported by said net.

30. The combination of claim 20 wherein said means for maintaining comprises an annular mass received about the outer surface of said container adjacent the open mouth thereof.

31. The combination of claim 30 wherein said sidewall of said container includes a peripheral flange portion providing an abutment for said annular mass.

32. The combination of claim 30 wherein said annular mass is secured to said outer surface of said container.

33. The combination of claim 20 further including inflatable flotation means carried by said container for rendering said container bouyant in said fluid.

34. The combination of claim 33 wherein said flotation means includes a tank storing gas under pressure, an inflatable member, and means for releasing said gas to the interior of said inflatable member.

35. The combination of claim 34 wherein said tank includes a closure member, and said releasing means includes means for opening said closure member.

36. The combination of claim 35 wherein said closure member comprises a rupturable disk and said opening means includes a translatable striking pin and means for translating said striking pin toward said disk.

37. The combination of claim 36 wherein said translating means includes an electrically operated solenoid.

38. The combination of claim 37 wherein said translating means further includes timing means carried by said container for energizing said solenoid after said predetermined time period has lapsed.

39. The combination of claim 37 wherein said translating means further includes means responsive to receipt of an externally generated acoustical signal for energizing said solenoid.

40. The combination of claim 20 wherein said container further includes means responsive to receipt of a first acoustic signal for generating a second acoustic signal to enable detection of the location of said container beneath said fluid body.

41. The combination of claim 20 wherein said container has a frusto-conical shape tapering inwardly from the open mouth thereof towards said bottom wall.

42. The combination of claim 20 wherein said container has a first body portion defining a first interior volume $V_1$ in which said means for obtaining a time integrated parameter is located, and a second body portion defining a second interior volume $V_2$ in communication with said volume $V_1$, and the ratio of said volumes being selected to prevent said fluid from contacting said means for obtaining said time integrated parameter when said container is positioned in situ.

43. The combination of claim 42 wherein said first and second body portions each has a generally cylindrical shape with the diameter of said first body portion being less than the diameter of said second body portion.

44. The combination of claim 20 wherein said container has a conical shape with an apex and a body altitude $A$.

45. The combination of claim 44 wherein said means for obtaining a time integrated parameter is mounted at a distance from said apex no greater than $$a_p = a \left( \frac{P_o}{P_x} \right)^{1/3}$$

where $P_o$ and $P_x$ are the atmospheric pressure and the hydrostatic pressure at a predetermined maximum design depth, respectively.

46. The combination of claim 20 further including means attached to said container for providing an observable indication of the location thereof in situ.

47. The combination of claim 46 wherein said providing means includes a buoyant device and a flexible line having a first portion secured to said container and a second portion secured to said buoyant device, the buoyancy of said buoyant device being insufficient to prevent said container from sinking in said fluid body to said surface of said earth region.

* * * * *